United States Patent [19]

Tanaka et al.

[11] Patent Number: 4,877,964
[45] Date of Patent: Oct. 31, 1989

[54] ULTRAVIOLET STERILIZING APPARATUS

[75] Inventors: Yoshio Tanaka; Shirou Saitou, both of Tokyo, Japan

[73] Assignee: Kureha Chemical Industry Co., Ltd., Tokyo, Japan

[21] Appl. No.: 221,229

[22] Filed: Jul. 19, 1988

[30] Foreign Application Priority Data

Aug. 5, 1987 [JP] Japan .............................. 62-119282[U]
Dec. 15, 1987 [JP] Japan .............................. 62-189377[U]

[51] Int. Cl.$^4$ ................................................ A61L 2/10
[52] U.S. Cl. ................................ 250/455.1; 250/453.1; 250/454.1; 250/492.1; 422/24
[58] Field of Search ................ 250/455.1, 454.1, 453.1, 250/504 R, 492.1; 34/4; 422/24

[56] References Cited

U.S. PATENT DOCUMENTS 2,095,502 10/1937 Johnston .......................... 250/454.1
2,275,788 3/1942 Meeker et al. .................... 250/455.1
4,055,769 10/1977 Sander .............................. 250/492.1

FOREIGN PATENT DOCUMENTS 3124335 1/1983 Fed. Rep. of Germany ... 250/504 R

Primary Examiner—Jack I. Berman
Attorney, Agent, or Firm—Rosen, Dainow & Jacobs

[57] ABSTRACT

An ultraviolet sterilizing apparatus includes a sterilization chamber defining an enclosed space and having an entrance and an exit, a roller conveyor arranged between the entrance and the exit for conveying products to be sterilized through the interior of the sterilization chamber, and a plurality of sterilizing ultraviolet lamps arranged about the path along which the products are conveyed. The apparatus is characterized in that some of the ultraviolet lamps are situated below the conveyance path, each of these ultraviolet lamps being interposed between mutually adjacent ones of the rollers in the roller conveyor and arranged far enough below the conveyance plane of the roller conveyor so as not to contact the products being conveyed. This ultraviolet lamp arrangement makes it possible to uniformly sterilize products over their entire surface without requiring that the products be turned over on the conveyor. The apparatus is further provided with auxiliary chambers each having an ultraviolet radiation shielding curtain suspended from an inlet and outlet of the apparatus to prevent ultraviolet rays from leaking out of the sterilization chamber.

5 Claims, 3 Drawing Sheets

ULTRAVIOLET STERILIZING APPARATUS

BACKGROUND OF THE INVENTION

1. Field of the Invention:

This invention relates to an ultraviolet sterilizing apparatus.

2. Description of the Prior Art:

An ultraviolet sterilizing apparatus is widely used to sterilize foodstuffs and other products requiring sterilization before or after being packaged. In order to continuously sterilize a large number of products, use is made of an apparatus of a type in which a conveyor is arranged to travel through the interior of a sterilizing chamber in which an ultraviolet lamp is housed. Since the sides of the products contacting the surface of the conveyor will not be irradiated with the ultraviolet rays, the products are conveyed while being repeatedly turned over on the conveyor, thus making it possible to irradiate the entire periphery of each product with ultraviolet rays. However, the mechanism for turning the products over is complicated, raises the cost of the apparatus and results in an apparatus of large size owing to the space required for installation of the mechanism. Shortcomings are also encountered in the results of sterilization. Specifically, since the products are irradiated with ultraviolet rays from a fixed direction only, products having uneven or irregular surfaces are not always perfectly irradiated over their entire surface merely by being turned over. As a result, the prescribed results are not always obtained.

Furthermore, since ultraviolet radiation is harmful to the eye, the conventional apparatus described above is provided with curtains, each comprising a plurality of strips hung from the openings to the entrance and exit through which the conveyor passes to travel through the sterilization chamber. However, when the products are conveyed in and out of the sterilization chamber, they force the aforementioned curtains aside and allow ultraviolet radiation to leak from the gaps between the curtain strips. As a result, the eyes of the operator handling the products are exposed to ultraviolet rays. Accordingly, there is need of a sterilizing apparatus capable of completely shutting out ultraviolet radiation from the outside during handling.

SUMMARY OF THE INVENTION

Accordingly, a first object of the present invention is to provide an ultraviolet sterilizing apparatus which is structurally simple and small in size, and in which products can be completely sterilized over their entire peripheral surface.

A second object of the present invention is to provide a highly safe ultraviolet sterilizing apparatus capable of completely preventing the leakage of ultraviolet rays from a sterilization chamber.

In accordance with the present invention, the first object of the invention is attained by providing an ultraviolet sterilizing apparatus comprising: a sterilization chamber defining an enclosed space and having an entrance and an exit; a roller conveyor including a number of rollers arranged between the entrance and the exit for conveying products to be sterilized through the interior of the sterilization chamber along a conveyance path; a plurality of first sterilizing ultraviolet lamps arranged about the conveyance path; and a plurality of second sterilizing ultraviolet lamps situated below the conveyance path, each of the second ultraviolet lamps being interposed between mutually adjacent ones of the rollers and arranged at a level lower than that of a conveyance plane of the roller conveyor. In a preferred embodiment, reflector plates are provided on the outer sides of the first and second ultraviolet lamps.

In accordance with the invention, the products conveyed on the roller conveyor have their upper surfaces and both side surfaces irradiated with ultraviolet radiation from the plurality of first ultraviolet lamps, and they also have their lower surfaces irradiated with ultraviolet radiation from the underlying plurality of second ultraviolet lamps each of which is disposed between a pair of rollers. Thus, each product has its entire peripheral surface fully irradiated even if the product is at rest on the roller conveyor. Since the plurality of second ultraviolet lamps are below the level of the roller conveyor plane, the products are not directly contacted by the lamps. If reflector plates are provided, the front and rear surfaces of the products, in terms of the conveyor traveling direction, are sterilized by ultraviolet rays from the reflectors, as well as by ultraviolet rays emitted when the products are conveyed in and out of the sterilization chamber.

If the products to be sterilized have uneven or irregular surfaces, portions lying in a shadow with respect to the direction of irradiation can be eliminated by providing the reflector plates with diffused reflector portions, as in a preferred embodiment of the invention. This will make it possible to sterilize such products over their entire surface. Though it is preferred that the entire area of the reflector plates exhibit diffused-type reflection, it will suffice if a portion of each reflector plate has such a capability. The reason for this is to maintain the tendency to produce diffused reflection even if the direction of diffused reflection is changed due to reflection by other flat surfaces.

In a case where the products to be sterilized have not yet been packaged, substances such as water sometimes emanate or evaporate from the products and attach themselves to the surfaces of the ultraviolet lamps, thereby causing a decline in lamp performance. In order to deal with such a situation, an arrangement can be adopted in which some of the ultraviolet lamps are grouped into several individual units and each unit is capable of being detached from and reattached to the apparatus independently of the other units. This is convenient in that it greatly facilitates maintenance.

Thus, in accordance with the invention as described above, the entire outer peripheral surfaces of products to be sterilized can be irradiated with ultraviolet radiation by means of a very simple ultraviolet lamp arrangement without requiring a special mechanism for repeatedly tuning the products over on the conveyor, as is necessary in the aforementioned prior ar. This contributes to a less costly and more compact apparatus. Furthermore, if the embodiment in which the reflector plates are rendered capable of diffused reflection is adopted, the foregoing effects are augmented by an ability to completely sterilize even irregularly shaped products by eliminating shadowed portion at the time of irradiation.

According to the present invention, the second object is attained by providing an ultraviolet sterilizing apparatus comprising: a sterilization chamber defining an enclosed space and having an entrance and an exit; a roller conveyor including a number of rollers arranged between the entrance and the exit for conveying products to be sterilized through the interior of the sterilization chamber along a conveyance path; a plurality of sterilizing ultraviolet lamps arrayed about the conveyance path; a first ultraviolet ray shielding curtain suspended from the entrance and from the exit; a first auxiliary chamber formed on an outer side of the entrance and having a carry-in port; a second auxiliary chamber formed on an outer side of the exit and having a carry-out port; and a second ultraviolet ray shielding curtain suspended from the carry-in port and from the carry-out port for allowing the products to be conveyed in and out of the first and second auxiliary chamber sand for shielding the first and second auxiliary chambers from the outside.

In accordance with this aspect of the invention, the products are received by the first auxiliary chamber before being fed into the sterilization chamber and enter the second auxiliary chamber upon exiting from the sterilization chamber following sterilization. Therefore, even if ultraviolet radiation should happen to leak from between the strips of the first curtains at the entrance and exit of the sterilization chamber, the same radiation is prevented from leaking to the outside by virtue of the second curtains provided at the carry-in and carry-out ports of the first and second auxiliary chambers, respectively. In other words, besides the shielding effect afforded by the double-curtain arrangement, a fully shielded state is maintained by the first curtains at the entrance and exit of the sterilization chamber or by the second curtains at the carry-in and carry-out ports of the auxiliary chambers, provided that the auxiliary chambers are larger in size than the products being sterilized. This positively eliminates leakage of ultraviolet radiation and assures complete shielding. If the rear side (inner side) of at least the first curtains or second curtains is coated with a a reflective layer of aluminum or the like, the aforementioned shielding effect can be enhanced. The firs and second curtains may comprise a sheet of glass fiber-reinforced polytetrafluoroethylene TEFLON, and plastic layers bonded to the top and bottom surfaces of the TEFLON sheet, these plastic layers serving as base layers on which a layer of aluminum may be formed by vapor deposition.

Thus, if the first and second auxiliary chambers respectively having the carry-in and carry-out ports are provided adjacent the entrance and exit of the sterilization chamber and the second curtains are suspended from the carry-in and carry-out ports in addition to the first curtains at the entrance and exit, not only is dual shielding effected when the products are conveyed in and out of the sterilization chamber, but complete shielding is also achieved by closure of the first curtains or closure of the second second at the carry-in port or carry-out port before and after the products are conveyed in and out of the sterilization chamber. Accordingly, leakage of ultraviolet radiation is positively eliminated to enhance safety with respect to the eyes of the operator.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
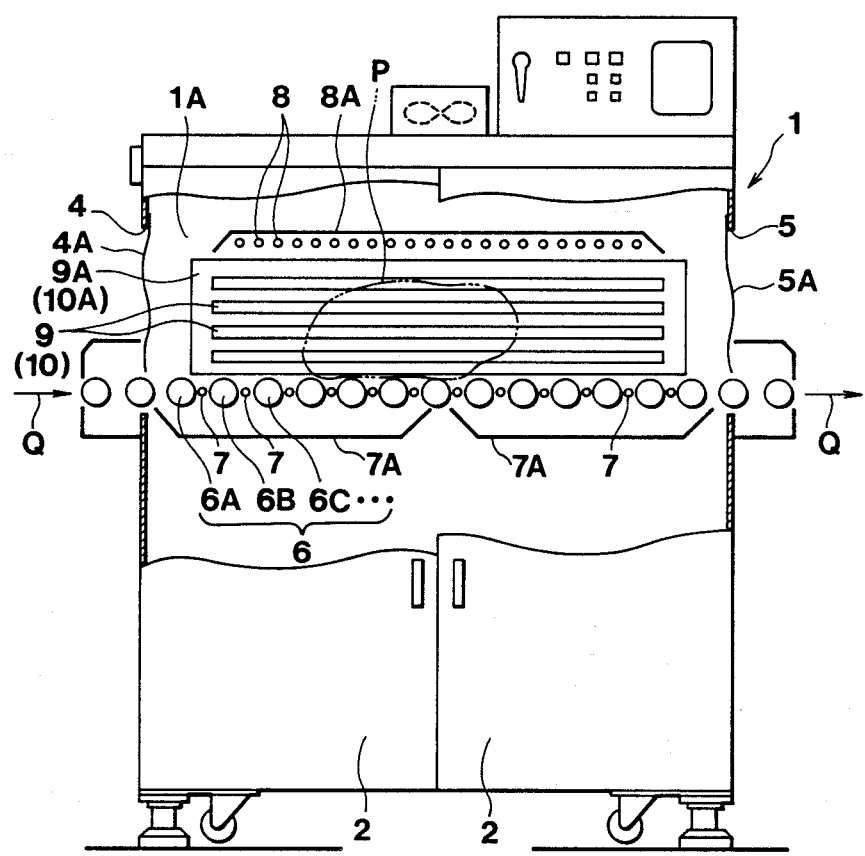
FIG. 1 is a front view, partially broken away, illustrating a first embodiment of an ultraviolet sterilizing apparatus according to the present invention.
Figure 2:
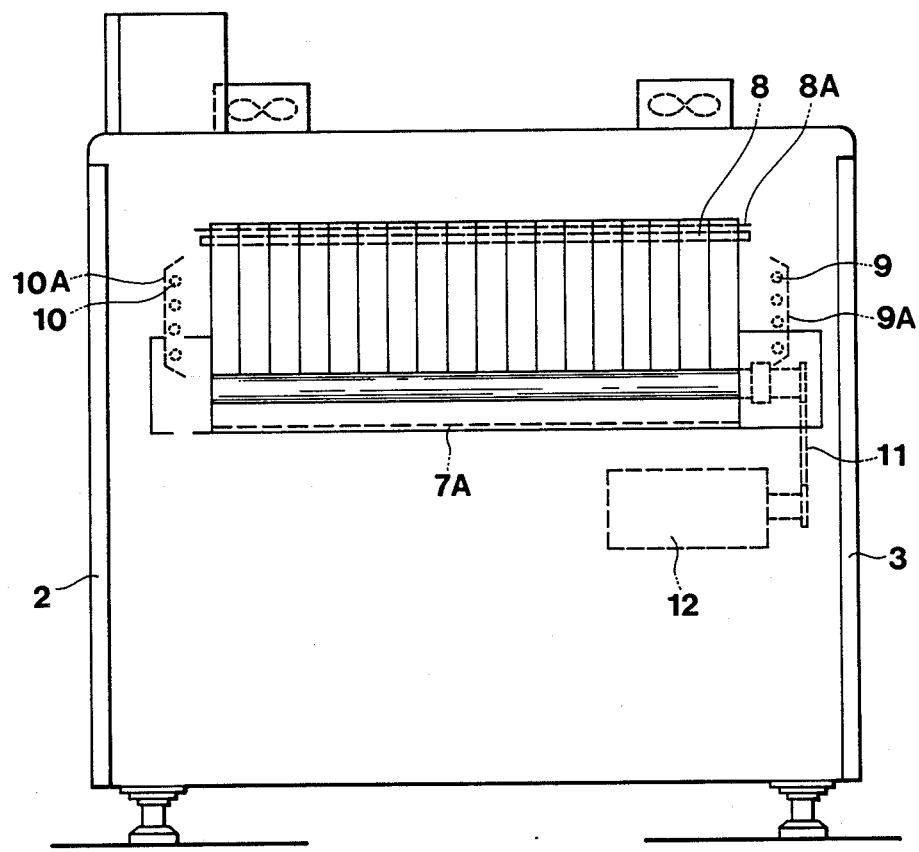
FIG. 2 is a side view of the apparatus shown in FIG. 1.

With reference first to FIGS. 1 and 2, there is shown an ultraviolet sterilizing apparatus 1 having front and back sides, respectively, provided with doors 2, 3 capable of being freely opened and closed. As shown in FIG. 1, the left side (by way of example) of the apparatus is formed to have an opening serving as an entrance 4, and the right side is formed to have an opening serving as an exit 5. A curtain 4A comprising a plurality of vertical strips is suspended at entrance 4, and a curtain 5A comprising a plurality of vertical strips is suspended at exit 5. These curtains 4A, 5A define an almost completely closed sterilization chamber 1A inside the apparatus.

A roller conveyor 6 comprising a number of rollers 6A, 6B, . . . extending from the front to the back of the apparatus (i.e. at right angles to the plane of the drawing) is disposed in a lane connecting the lower portions of the entrance 4 and exit 5. The rollers 6A, 6B, . . . are rotatively driven simultaneously by a motor 12 acting through a chain 11 or the like (see FIG. 2). An ultraviolet lamp 7 is disposed between mutually adjacent ones of those rollers 6A, 6B that are located within the sterilization chamber 1A. The ultraviolet lamps 7 are arranged below the conveyance plane of the roller conveyor 6, namely below a common straight line contacting the rollers on their upper side, and the ultraviolet lamps 7 are kept out of contact with the rollers.

A plurality of ultraviolet lamps 8, 9, 10 are provided above the roller conveyor 6 and at both the front and back thereof so as to cooperate with the aforementioned lower ultraviolet lamps 7 in surrounding a product P to be sterilized. The ultraviolet lamps 7, 8, 9 and 10 preferably have a wavelength near 260 mm, which is the wavelength having the strongest sterilizing effect. However, the wavelength can be set appropriately when taking the products, the size of the apparatus and the relationship between them into consideration.

Reflector plates 7A, 8A, 9A and 10A are disposed just outboard of the ultraviolet lamps 7, 8, 9 and 10, respectively, The edge portions of these reflector plates are bent inwardly to reflect the ultraviolet rays toward the center of the sterilization chamber 1A. Preferably, at least one of the reflector plates has a surface configuration for diffused reflection of the ultraviolet radiation. Also, the ultraviolet reflectors 7, 8, 9 and 10 are grouped into respective units, each of which is capable of being freely attached to and detached from the apparatus.

Sterilization performed by the apparatus of the present embodiment will now be described.

If the roller conveyor 6 is driven for conveyance purposes in the direction indicated by arrow Q, the product P to be sterilized will be conveyed in from the entrance 4 through the curtain 4A. Upon passing through the curtain 4A, the product P is conveyed successively in the direction Q on the rollers 6A, 6B . . . that are being rotated simultaneously. From the moment the product P enters from entrance 4 until it leaves from exit 5, each surface of the product is irradiated and sterilized by the ultraviolet lamps 7, 8, 9 and 10. Even though the product is stationary on the roller conveyor 6, the bottom surface of the product is irradiated by the ultraviolet lamps 7 of which are disposed between a pair of the rollers of the roller conveyor 6. Furthermore, since the ultraviolet rays emitted by the ultraviolet lamps 7, 8, 9 and 10 are reflected by the respective reflector plates 7A, 8A, 9A and 10A, the rate of irradiation is improved. Even the front and rear surfaces of the product P are sterilized due to the ultraviolet rays reflected from the curved portions at the front and rear edges of the reflector plates. If the reflector plates are adapted for diffused reflection, even a product having an irregular surface can be effectively irradiated since portions that would otherwise lie in a shadow with respect o the ultraviolet irradiation are eliminated.

The ultraviolet sterilizing apparatus of the invention is convenient in terms of maintenance as well. Specifically, when the apparatus is used over an extended period of time, deposits tend to built up on the ultraviolet lamps due to substances such as water which fall off the product before it is packaged. With the apparatus of the invention, the arrangement is preferably such that the individual ultraviolet lamp units, each comprising a plurality of ultraviolet lamps, can be extracted periodically from the apparatus independently of one another by opening the front and back doors 2, 3. Following washing, the units can be remounted inside the apparatus through the doors 2, 3. Thus, periodic washing and maintenance are facilitated.

A second embodiment of the invention will now be described with reference to FIG. 3. Portions similar to those of the first embodiment shown in FIGS. 1 and 2 are denoted by like reference characters and need not be described again.

In accordance with this embodiment, box-shaped auxiliary chambers 20, 21 are attached to the outer side of the entrance 4 and exit 5, respectively. The auxiliary chambers 20, 21 are provided with a carry-in port 22 and carry-out port 23, respectively, at positions corresponding to the entrance 4 and exit 5. Curtains 22A, 23A each comprising a plurality of vertical strips and similar to those described above are suspended so as to substantially close the carry-in port 22 and carry-out port 23, respectively. At least one of the curtains 4A and 22A, and at least one of the curtains 5A, 23A, preferably has its rear (inner) side coated with a substance, such as aluminum, capable of reflecting ultraviolet radiation.

Though the size of the interior space of each of the auxiliary chambers 20, 21 is considered to be adequate, in this embodiment the size is set to be larger than at least the size (particularly the dimension in the direction of conveyance) of the product that is expected to be sterilized.

Figure 3:
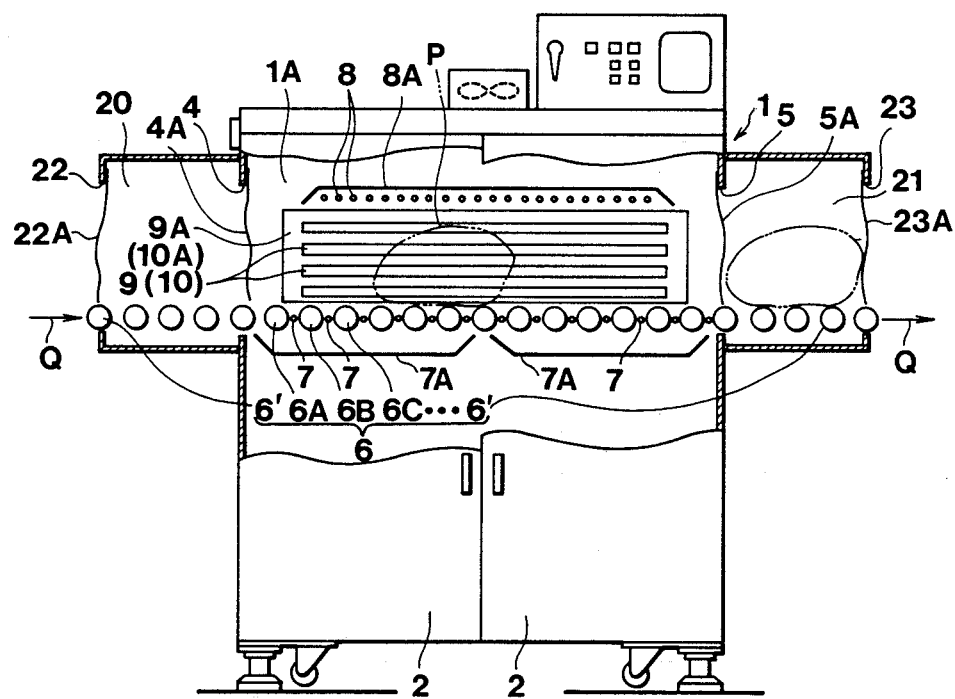
FIG. 3 is a front view, partially broken away, illustrating a second embodiment of an ultraviolet sterilizing apparatus according to the present invention.

As shown in FIG. 3, the roller conveyor 6 is disposed in a plane connecting the lower portions of the carry-in port 22 and carry-out port 23 and comprises rollers arranged to extended from the front to the back sides of the apparatus (i.e. at right angles to the plane of the drawing of FIG. 3). (The rollers within the sterilization chamber 1A are denoted by 6A, 6B, . . . , and those external to the sterilization chamber 1A are denoted by numeral 6'.) As in the first embodiment described above, the rollers are rotatively driven simultaneously by a motor acting through a chain or the like. Also, as in the first embodiment, the ultraviolet lamp 7 is disposed between mutually adjacent ones of those rollers 6A, 6B that are located within the sterilization chamber 1A, and the ultraviolet lamps 7 are arranged below the conveyance plane of the roller conveyor 6 and are kept out of contact with the rollers.

If the roller conveyor 6 in this embodiment of the apparatus is driven for conveyance purposes in the direction indicated by arrow Q, the product P to be sterilized will first be conveyed into the auxiliary chamber 20 from the carry-in port 22 through the curtain 22A. Upon passing through the curtain 22A, the product P is conveyed successively in the direction Q on the rollers 6', . . . , 6A, 6B . . . that are being rotated simultaneously. When the product P pushes aside the curtain 4A and enters the sterilization chamber 1A, any ultraviolet radiation that may leak out from the gap between the strips of the curtain 4A is completely cut off from the outside of the apparatus by the closed curtain 22A at the carry-in port 22. From the moment the product P enters from the entrance 4 until it leaves from exit 5, each surface of the product is irradiated and sterilized by the ultraviolet lamps, as in the first embodiment.

The product P, fully sterilized within the sterilization chamber 1A, is conveyed out of the apparatus first through the exit 5 and then through the carry-out port 23. As at the time of carry-in, when the sterilized product P pushes aside the curtain 5A or 23A, the other one of these two curtains is completely closed and, hence, there is no leakage of ultraviolet radiation to the outside.

In the above embodiment, the roller conveyor 6 passes though the auxiliary chambers 20, 21 and extends beyond these chambers to points outside the apparatus. However, it is of course possible to adopt an arrangement in which products are carried to the inlet of auxiliary chamber 20 by hand, to then be conveyed inward and retrieved from the outlet of auxiliary chamber 21 by hand.

As many apparently widely different embodiments of the invention can be made without departing from the spirit and scope thereof, it is to be understood that the invention is not limited to the specific embodiments thereof except as defined in the appended claims.

What is claimed is:
1. An ultraviolet sterilizing apparatus comprising:
    a sterilization chamber defining an enclosed space and having an entrance and an exit;
    a roller conveyor including a number of rollers arranged between the entrance and the exit for conveying products to be sterilized through the interior of said sterilization chamber along a conveyance path;
    a plurality of first sterilizing ultraviolet lamps arranged about the conveyance path; and
    a plurality of second sterilizing ultraviolet lamps situated below the conveyance path, each of said second ultraviolet lamps being interposed between mutually adjacent ones of said rollers and arranged at a level lower than that of a conveyance plane of said roller conveyor.

2. The apparatus according to claim 1, wherein said ultraviolet lamps are mounted within said sterilization chamber upon being divided into a plurality of individual units, each unit being freely attachable to and detachable from said apparatus.

3. The apparatus according to claim 1, wherein reflector plates are provided on outer peripheral sides of said ultraviolet lamps.

4. The apparatus according to claim 3, wherein said reflector plates have a diffused-type reflector surface at least on a portion thereof.

5. An ultraviolet sterilizing apparatus comprising:
- a sterilization chamber defining an enclosed space and having an entrance and an exit;
- a roller conveyor including a number of rollers arranged between the entrance and the exit for conveying products to be sterilized through the interior of said sterilization chamber along a conveyance path;
- a plurality of sterilizing ultraviolet lamps arrayed about the conveyance path;
- a first ultraviolet ray shielding curtain suspended from the entrance and from the exit;
- a first auxiliary chamber formed on an outer side of the entrance and having a carry-in port;
- a second auxiliary chamber formed on an outer side of the exit and having a carry-out port;
- a second ultraviolet ray shielding curtain suspended from the carry-in port and from the carry-out port for allowing the products to be conveyed in and out of said first and second auxiliary chambers and for shielding said first and second auxiliary chambers from the outside; and
- said plurality of ultraviolet lamps including lower ultraviolet lamps situated below the conveyance path, each of said lower ultraviolet lamps being disposed between mutually adjacent ones of said rollers at a level far enough below a conveyance plane of said roller conveyor so as to be kept out of contact with the products conveyed.

* * * * *